US009598936B1

(12) United States Patent
Gao et al.

(10) Patent No.: US 9,598,936 B1
(45) Date of Patent: Mar. 21, 2017

(54) APPARATUS AND METHOD FOR MONITORING HYDRATE DECOMPOSITION AREA UNDER DIFFERENT DRILLING AND PRODUCTION PROCESSES

(71) Applicant: China University of Petroleum (East China), Qingdao, Shandong (CN)

(72) Inventors: Yonghai Gao, Shandong (CN); Ye Chen, Shandong (CN); Baojiang Sun, Shandong (CN); Wenchao Sun, Shandong (CN); Hao Li, Shandong (CN)

(73) Assignee: China University Of Petroleum (East China), Shandong (CN)

( * ) Notice: Subject to any disclaimer, the term of this patent is extended or adjusted under 35 U.S.C. 154(b) by 0 days.

(21) Appl. No.: 15/270,571

(22) Filed: Sep. 20, 2016

(30) Foreign Application Priority Data

Oct. 12, 2015 (CN) .......................... 2015 1 0657568

(51) Int. Cl.
*G01N 33/24* (2006.01)
*E21B 41/00* (2006.01)
(Continued)

(52) U.S. Cl.
CPC .............. *E21B 41/00* (2013.01); *E21B 43/34* (2013.01); *E21B 47/06* (2013.01); *E21B 47/065* (2013.01);
(Continued)

(58) Field of Classification Search
CPC ......... E21B 43/24; E21B 43/164; E21B 21/00
See application file for complete search history.

(56) References Cited

U.S. PATENT DOCUMENTS

2015/0205004 A1* 7/2015 Li ........................ G01V 99/005
703/10

FOREIGN PATENT DOCUMENTS

CN 101042387 A 9/2007
CN 101451985 A 6/2009
(Continued)

OTHER PUBLICATIONS

Deusner, C. et al. Methane Production from Gas Hydrate Deposits through Injection of Supercritical CO2, 2012, Energies, vol. 5, pp. 2112-2140.*

(Continued)

*Primary Examiner* — Robert Xu
(74) *Attorney, Agent, or Firm* — Calfee, Halter & Griswold LLP

(57) ABSTRACT

The present invention relates to an apparatus and a method for monitoring a hydrate decomposition area under different drilling and production processes. The apparatus for monitoring hydrate decomposition area under different drilling and production processes comprises a reaction unit, an auxiliary unit and a determination unit; the reaction unit is used to simulate the hydrate storage layer environment, provide a place for generation and decomposition of a hydrate, simulate a hydrate heat-injection exploitation process, a hydrate pressure-reduction exploitation process and a hydrate $CO_2$ displacement exploitation process, and also analyze the hydrate decomposition status at various areas by calculating the hydrate decomposition rate, thereby evaluating and optimizing the drilling and production process; the auxiliary unit is used to provide a gas source and a liquid source for the reaction unit, and simulate different hydrate drilling and production processes; and the determination unit is used to measure the hydrate decomposition rate in different drilling and production processes.

9 Claims, 2 Drawing Sheets

(51) Int. Cl.
*E21B 43/34* (2006.01)
*E21B 47/06* (2012.01)
*G01N 33/22* (2006.01)
*E21B 43/24* (2006.01)
*E21B 43/16* (2006.01)
*E21B 21/00* (2006.01)

(52) U.S. Cl.
CPC ............ *G01N 33/225* (2013.01); *E21B 21/00* (2013.01); *E21B 43/164* (2013.01); *E21B 43/24* (2013.01)

(56) References Cited

FOREIGN PATENT DOCUMENTS

| CN | 201747338 | * | 2/2011 | ............ E21B 43/01 |
|---|---|---|---|---|
| CN | 101575964 | * | 4/2013 | ............ E21B 43/01 |
| CN | 104360021 | * | 2/2015 | ............ G01N 33/00 |
| CN | 104453794 | * | 3/2015 | ............ E21B 47/00 |
| JP | 200499846 A | | 4/2004 | |

OTHER PUBLICATIONS

English Translation of Notice of Allowance from Chinese Patent Application No. 201510657568.5 dated Aug. 1, 2016.

* cited by examiner

APPARATUS AND METHOD FOR MONITORING HYDRATE DECOMPOSITION AREA UNDER DIFFERENT DRILLING AND PRODUCTION PROCESSES

CROSS REFERENCE TO RELATED APPLICATIONS

This application claims priority to Chinese Application No. 201510657568.5, filed on Oct. 12, 2015, entitled "Apparatus and method for monitoring hydrate decomposition area under different drilling and production processes", which is specifically and entirely incorporated by reference.

TECHNICAL FIELD

The present invention belongs to the field of natural gas exploitation, and specifically relates to an apparatus and a method for monitoring a hydrate decomposition area under different drilling and production processes, which can simulate the three processes for drilling and production of hydrate such as heat-injection exploitation, pressure-reduction exploitation and $CO_2$ displacement exploitation, and judge the decomposition of the hydrate in different areas by monitoring and analyzing the impedance, temperature, pressure and image data, thereby evaluating and optimizing different drilling and production processes.

BACKGROUND

The natural gas hydrate is a future clean energy mainly consisting of methane and water, which is widely distributed in the Eastern and Western Pacific Ocean and at the western margin of the Atlantic Ocean. Its giant reserves and less pollution after combustion attracted attention of specialists in various countries in the energy field. Since marine exploitation is much more difficult than land exploitation, plenty of natural gas hydrate is still stored in the seabed and the permafrost up to now.

Risks exist with exploitation of the natural gas hydrate. Once blowout accident occurs, it might cause disasters such as tsunami, submarine landslide, seawater poisoning and the like. In addition, the presence of the natural gas hydrate might cause the seabed to be unstable, leading to large-scale submarine mudflow and causing severe damage to submarine pipeline and communication cables. If the submarine layer is broken in an earthquake, the gas generated by decomposition of the natural gas hydrate is ejected out of the sea surface, or a large amount of inflammable bubbles is formed on the seawater surface layer, which poses threat to the passing ships or even low-altitude flying airplanes. Therefore, during exploiting the natural gas hydrate, risk accidents should be prudently avoided.

Currently, three methods for exploiting the natural gas hydrate have been proposed: heat-injection, pressure-reduction and displacement processes. The heat-injection process includes decomposing methane steam in a heat injection manner by using the thermolabile characteristic of the natural gas hydrate. The pressure-reduction process uses the labile characteristic of the natural gas hydrate during depressurization. However, since the porous media in the submarine are not concentrated but evenly distributed, the decomposed natural gas is not easy to be collected, and how to arrange the pipelines and efficiently collect are problems to be solved in the art. The displacement method normally uses $CO_2$ gas. As the ability of $CO_2$ for forming the hydrate is stronger than $CH_4$, under massive injection, it is possible to displace $CH_4$ in the natural gas hydrate to reach the aim of exploitation. How to set reasonable temperature and pressure parameter range in the exploitation to avoid accident occurrence is the problem to be solved in the actual production.

Targeting to the above-mentioned situation, it is necessary to design a set of methods capable of simulating drilling and exploiting the hydrate layer indoors, and an apparatus for monitoring and analyzing the stratum parameter in the exploitation to optimize the exploitation method of natural gas hydrate under different environments, thereby predicting and evaluating the problem and risk in the actual production.

SUMMARY OF THE INVENTION

In order to analyze and evaluate the drilling process and the existing natural gas exploitation technology, the present invention provides an apparatus and a method for monitoring hydrate decomposition area under different drilling and production processes for simulating drilling process, heat-injection, pressure-reduction and displacement processes and an apparatus and a method for monitoring hydrate decomposition area in the exploitation process, so as to provide basis for actual application of exploiting natural gas hydrate in the deep water exploration and production.

In order to solve the above-mentioned technical problem, the present invention applies the technical solution as follows:

The apparatus for monitoring hydrate decomposition area under different drilling and production processes comprises a reaction unit, an auxiliary unit and a determination unit; the reaction unit is used to simulate the hydrate storage layer environment, provide a place for generation and decomposition of a hydrate, simulate a hydrate heat-injection exploitation process, a hydrate pressure-reduction exploitation process and a hydrate $CO_2$ displacement exploitation process, and also analyze the hydrate decomposition status at various areas by calculating the hydrate decomposition rate, thereby evaluating and optimizing the drilling and production process; the auxiliary unit is used to provide a gas source and a liquid source for the reaction unit, and simulate different hydrate drilling and production processes; and the determination unit is used to measure the hydrate decomposition rate in different drilling and production processes.

Compared with the prior arts, the present invention provides the beneficial effects as follows: capable of simulating the effects of different hydrate drilling and production processes, and optimizing the corresponding parameters, specifically including:

1. It can simulate pressure-reduction process for exploiting hydrate, calculate the exploitation rate, analyze hydrate decomposition status in various areas and optimize the pressure-reduction process by changing the corresponding parameter;
2. It can simulate heat-injection process for exploiting hydrate, calculate the exploitation rate, analyze hydrate decomposition status in various areas and optimize the heat injection process by changing the corresponding parameter;
3. It can simulate methane-displaced-with-carbon dioxide process for exploiting hydrate, calculate the exploitation rate, analyze hydrate decomposition status in various areas and optimize the displacement process by changing the corresponding parameters;
4. It can simulate the decomposition area of the hydrate layer in the exploitation process of the hydrate storage layer and controls the decomposition of the hydrate storage layer during drilling by changing the corresponding parameters.

In the figures, 101, incubator; 102, reactor; 103, air inlet; 104, air outlet; 105, liquid inlet; 106, support; 107, drill pipe; 108, slurry pump; 109, flow gauge; 110, check valve; 111, impedance sensor; 112, return pipeline; 201, vacuum pump; 202, vacuum gauge; 203, high pressure methane gas cylinder; 204, high pressure carbon dioxide gas cylinder; 205, gas booster pump; 206, liquid injection apparatus; 207, constant pressure and constant speed pump; 208, heating apparatus; 301, pressure regulating valve; 302, gas-liquid separator device; 303, closed liquid drainage container; 304, weighing apparatus; 305, thermal insulation gas storage cylinder; 306, three-way valve; 401, first liquid storage container; 402, second liquid storage container; 403, third liquid storage container; 404, fourth liquid storage container; 501, first control valve; 502, second control valve; 503, third control valve; 504, fourth control valve; 601, first pressure sensor; 602, second pressure sensor; 603, third pressure sensor; 604, fourth pressure sensor; 605, fifth pressure sensor; 701, first temperature sensor; 702, second temperature sensor; 801, first pin valve; and 802, second pin valve.

DETAILED DESCRIPTION

Figure 1:
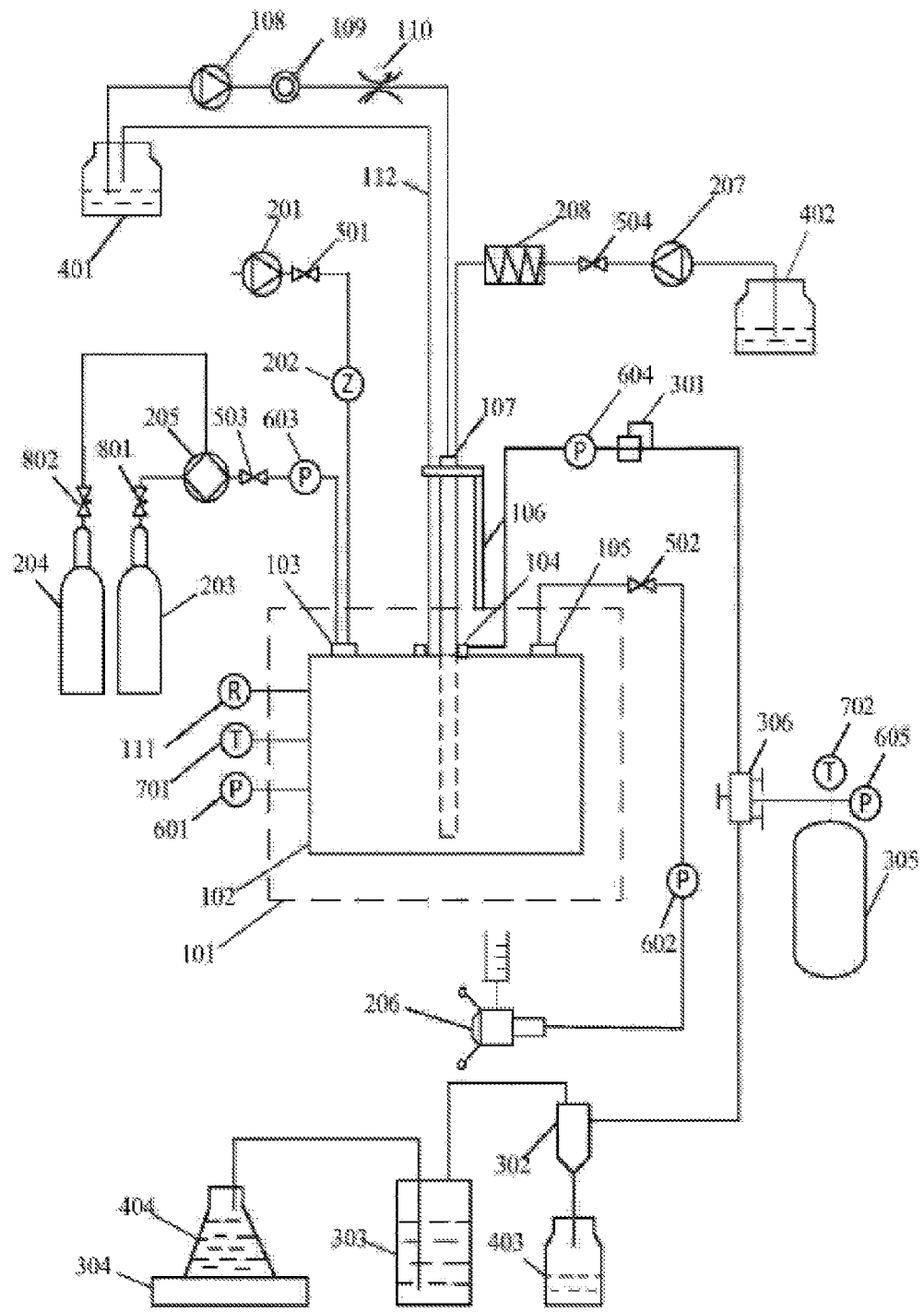
FIG. 1 is a schematic diagram of an apparatus for monitoring hydrate decomposition area under different drilling and production processes.

As shown in FIG. 1, the apparatus for monitoring hydrate decomposition area under different drilling and production processes comprises a reaction unit, an auxiliary unit and a determination unit; the reaction unit is used to simulate the hydrate storage layer environment to provide a place for generation and decomposition of a hydrate, simulate a hydrate heat-injection exploitation process, a hydrate pressure-reduced exploitation process and a hydrate $CO_2$ displacement exploitation process, and also analyze the hydrate decomposition status at various areas by calculating the hydrate decomposition rate, thereby evaluating and optimizing the drilling and production process; the auxiliary unit is used to provide a gas source and a liquid source for the reaction unit, and simulate different hydrate drilling and production processes; and the determination unit is used to measure the hydrate decomposition rate in different drilling and production processes.

The reaction unit includes an incubator 101, a reactor 102, a drill pipe 107 and a first liquid storage container 401. The reactor 102 is disposed inside the incubator 101. A support 106 is disposed on the top of the incubator 101 for clamping the drill pipe 107. The reactor 102 contains the required sand to simulate the actual hydrate storage layer. The temperature of the incubator 101 is controllable to simulate a storage layer environment with different temperatures. The drill pipe 107 provides a channel for circulation of the slurry drilling liquid.

An air inlet 103, a liquid inlet 105 and an air outlet 104 are formed on the top end of the reactor 102 with the air outlet 104 located at the center and the air inlet 103 and the liquid inlet 105 located on two sides of the air outlet 104. The drill pipe 107 enters into the reactor 102 through the air outlet 104.

The first liquid storage container 401 is connected with the top end of the drill pipe 107 through a transmission pipeline. A slurry pump 108, a flow gauge 109 and a check valve 110 are orderly disposed on the transmission pipeline in a direction from the first liquid storage container 401 to the drill pipe 107. The air outlet 104 is connected with the first liquid storage container 401 through a return pipeline 112. The first liquid storage container 401 contains the slurry drilling liquid that passes through the flow gauge 109 for measuring the actual flow rate and enters into the drill pipe 107 by pumping through the slurry pump 108. The check valve 110 controls the flow direction of the slurry drilling liquid. The slurry drilling liquid is circulated back to the first liquid storage container 401 through the return pipeline 112.

Figure 2:
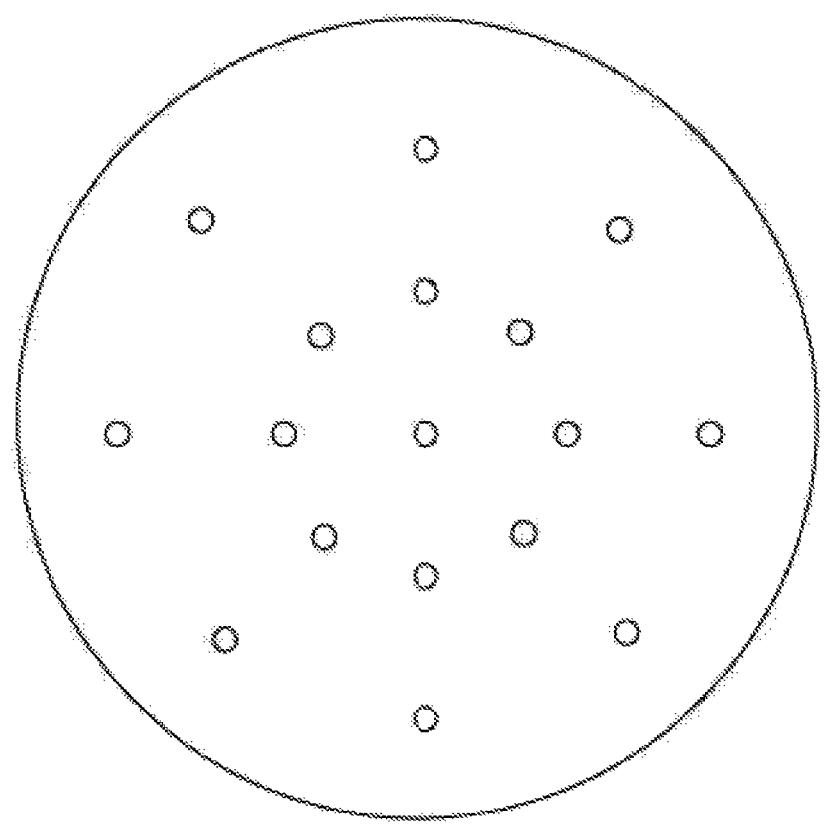
FIG. 2 is a schematic diagram showing distribution of impedance sensors on each layer within a reactor 102.

The reactor 102 is provided with impedance sensors 111, a first pressure sensor 601 and a first temperature sensor 701 that are connected with a computer data processing system. As shown in FIG. 2, the impedance sensors 111 are longitudinally and uniformly distributed inside the reactor 102 in three layers with 17 in each layer. One impedance sensor is disposed at the center of each layer. Eight radial directions extend by taking the impedance sensor at the center as the starting point. The adjacent radial directions form an angle of 45 degrees. Two impedance sensors are disposed equidistantly in each radial direction except the one at the center, i.e., except the one at the center, the remaining impedance sensors are located on two concentric circles so as to monitor generation and decomposition of the hydrate in various areas. The impedance sensor 111 measures the real-time impedance within the reactor 102, the first pressure sensor 601 measures the real-time pressure within the reactor 102, and the first temperature sensor 701 measures the real-time temperature within the reactor 102.

The auxiliary unit includes a vacuum pump 201, a vacuum gauge 202, a high pressure methane gas cylinder 203, a high pressure carbon dioxide gas cylinder 204, a gas booster pump 205, a liquid injection apparatus 206, a second liquid storage container 402 and a heating apparatus 208. The vacuum pump 201 is connected with the air inlet 103 through a pipeline. A first control valve 501 and the vacuum gauge 202 are installed orderly on the pipeline in a direction from the vacuum pump 201 to the air inlet 103. Before the monitoring operation, the vacuum pump 201 vacuumizes the reactor 102, the first control valve 501 controls the flow of the gas, and the vacuum gauge 202 measures the condition of vacuumizing within the reactor 102. The gas booster pump 205 is connected with the air inlet 103 through the transmission pipeline. A third control valve 503 and a third pressure sensor 603 are installed orderly on the transmission pipeline in a direction from the gas booster pump 205 to the air inlet 103. The gas booster pump 205 pressurizes the gas to the preset value and inputs it into the reactor 102. The third control valve 503 is used to control the condition of the gas flow. The third pressure sensor 603 measures the actual pressure of the gas.

The high pressure methane gas cylinder 203 is provided with a first pin valve 801 that is connected with the gas booster pump 205 through the transmission pipeline. A high pressure methane gas is stored in the high pressure methane gas cylinder 203 for providing a gas source for a hydrate generation and decomposition unit. The first pin valve 801 controls the in and out of the methane gas in the high pressure methane gas cylinder 203.

The high pressure carbon dioxide gas cylinder 204 is provided with a second pin valve 802 that is connected with the gas booster pump 205 through the transmission pipeline. A high pressure carbon dioxide gas is stored in the high pressure carbon dioxide gas cylinder 204 for providing a gas source for simulating natural gas hydrate drilling and production using a displacement method. The second pin valve 802 controls the in and out of the carbon dioxide gas in the high pressure carbon dioxide gas cylinder 204.

The liquid injection apparatus 206 is connected with the liquid inlet 105 on the reactor 102 through the transmission pipeline. A second pressure sensor 602 and a second control valve 502 are installed orderly on the transmission pipeline in a direction from the liquid injection apparatus 206 to the liquid inlet 105. The liquid injection apparatus 206 consists of a liquid communicating vessel and a manual pump. The liquid communicating vessel contains a set disposing solution; and the disposing solution is injected into the reactor 102 through the manual pump. The second control valve 502 controls the flow of the injected solution, and the second pressure sensor 602 measures the real-time pressure of the injected solution.

The second liquid storage container 402 is connected with the top end of the drill pipe 107 through the transmission pipeline. A constant pressure and constant speed pump 207, a fourth control valve 504 and the heating apparatus 208 are installed orderly on the transmission pipeline in a direction from the second liquid storage container 402 to the drill pipe 107. The second liquid storage container 402 contains the set solution to simulate the hydrate drilled and produced by the heat-injection process. The solution is pumped through the constant pressure and constant speed pump 207, heated by the heating apparatus 208 to the preset temperature and then enters into the reactor 102 through the drill pipe 107. The fourth control valve 504 is used to control the flow of the solution.

The determination unit includes: a pressure regulating valve 301, a gas-liquid separator apparatus 302, a closed liquid drainage container 303, a weighing apparatus 304, a pre-vacuumed thermal insulation gas storage cylinder 305, and a three-way valve 306. The air outlet 104 is connected with the three-way valve 306 through the transmission pipeline. A fourth pressure sensor 604 and the pressure regulating valve 301 are installed orderly on the transmission pipeline in a direction from the air outlet 104 to the three-way valve 306. The fourth pressure sensor 604 measures the real-time pressure within the reactor 102 when discharging the gas. The pressure regulating valve 301 is regulated to keep the real-time pressure within the reactor 102 at a set fixed value. The flow and the flow direction of the fluid are controlled through the three-way valve 306. The gas-liquid separator apparatus 302 is connected with the three-way valve 306. The three-way valve 306 guides the discharged fluid to the gas-liquid separator apparatus 302 for gas-liquid separation. A liquid hole is formed on the lower part of the gas-liquid separator apparatus 302. The liquid hole is connected with the third liquid storage container 403 through the transmission pipeline. The third liquid storage container 403 contains the separated liquid. An air hole is formed on the upper end of the gas-liquid separator apparatus 302. The air hole is connected with the top end of the closed liquid drainage container 303 through the transmission pipeline. The closed liquid drainage container 303 is connected with the fourth liquid storage container 404 through the transmission pipeline. The transmission pipeline stretches into the inner chamber of the closed liquid drainage container 303 and approaches to the bottom. The fourth liquid storage container 404 is placed on the weighing apparatus 304. The weighing apparatus 304 is connected with the computer data processing system. The closed liquid drainage container 303 measures the volume of the gas after gas-liquid separation through a drainage process. The fourth liquid storage container 404 contains water discharged through the drainage process. The weighing apparatus 304 measures the mass of the discharged water. The computer data processing system is used to collect, store and analyze the real-time mass data. The pre-vacuumed thermal insulation gas storage cylinder 305 is connected with the three-way valve 306 through the transmission pipeline. The thermal insulation gas storage cylinder 305 is equipped with a second temperature sensor 702 and a fifth pressure sensor 605. The volume of the thermal insulation gas storage cylinder 305 is constant to change the pressure of the system and simulate the hydrate pressure-reduction exploitation process. The second temperature sensor 702 and the fifth pressure sensor 605 measure the real-time temperature and pressure within the thermal insulation gas storage cylinder 305.

The vacuum pump 201 vacuumizes the reactor 102. The methane gas and the prepared solution are injected into the reactor 102 through the gas booster pump 205 and the liquid injection apparatus 206. The power supply of the incubator 101 is turned on to set the temperature to simulate generation of the hydrate. When the pressure within the reactor 102 reaches the preset value, and the generation of the hydrate becomes stable, the slurry pump 108 is opened to simulate circulation of the slurry drilling liquid. The hot fluid is injected into the reactor 102 using the constant pressure and constant speed pump 207 and the heating apparatus 208 to simulate hydrate heat-injection exploitation. The thermal insulation gas storage cylinder 305 is communicated with the reactor 102 to simulate hydrate pressure-reduction exploitation. Carbon dioxide is injected into the reactor 102 by using the gas booster pump 205 to simulate hydrate displacement exploitation. The gas-liquid separator apparatus 302, the closed liquid drainage container 303 and the fourth liquid storage container 404 are used to perform measurement of the drainage process to calculate the decomposition rate of the hydrate under different drilling and production processes.

A method for monitoring hydrate decomposition area under different drilling and production processes uses the above-mentioned apparatus for monitoring hydrate decomposition area under different drilling and production processes to simulate generation of hydrate, a hydrate pressure-reduction exploitation process under a slurry circulation condition, a hydrate heat-injection exploitation process under the slurry circulation process and a hydrate methane-displaced-with-carbon dioxide exploitation process under the slurry circulation condition.

Simulating generation of hydrate includes the specific steps as follows:

Placing quantitative sand and stone in the reactor 102 according to the set proportion and distribution to simulate the corresponding storage layer environment, closing all the valves of the apparatus;

Opening the first control valve 501 and the vacuum pump 201 to pump out the gas in the inner chamber of the reactor 102 until the reading of the vacuum gauge 202 is negative.

Closing the vacuum pump 201 and the first control valve 501;

Preparing an ionic solution with a specified concentration and putting it in the liquid communicating vessel of the liquid injection apparatus 206;

Opening the second control valve 502; rotating a manual pump in the liquid injection apparatus 206 to inject the prepared solution into the reactor 102; during the injection process, adjusting the rotating speed of the manual pump by observing the pressure reading of the second pressure sensor 602, observing and recording the volume reading on the liquid communicating vessel until the pressure reading of the second pressure sensor 602 and the volume reading of the liquid communicating vessel reach the preset value; stopping rotating the manual pump and closing the second control valve 502;

Turning on a power supply of the incubator 101, adjusting the temperature to the preset value, and heating the reactor 102 until the actual reading change of the temperature of the incubator 101 is less than plus or minus 0.01° C.;

Opening the first pin valve 801 and the third control valve 503, opening the gas booster pump 205, setting a specified pressure, pumping the methane gas within the high pressure methane gas cylinder 203 to the reactor 102, observing and recording the real-time readings of the first pressure sensor 601, the third pressure sensor 603, the impedance sensor 111 and the first temperature sensor 701; continuing gas injection until the readings of the first pressure sensor 601 and the third pressure sensor 603 reach the preset value and the readings of the impedance sensor 111 and the first temperature sensor 701 become stable, i.e., after the hydrate within the reactor 102 is generated completely under the preset pressure, closing the first pin valve 801 and the third control valve 503 and closing the gas booster pump 205.

Simulating a hydrate pressure-reduction exploitation process under a slurry circulation condition includes the specific steps as follows:

After simulating generation of the hydrate, recording the reading of the first pressure sensor 601 as $P_1$, and opening the slurry pump 108 to form a slurry circulation system.

Opening the valve on the three-way valve 306 that is connected with the reactor 102 and the thermal insulation gas storage cylinder 305 so that the thermal insulation gas storage cylinder 305 is communicated with the inner chamber of the reactor 102, thereby realizing a pressure reduction function; observing and recording readings on the fourth pressure sensor 604, the fifth pressure sensor 605 and the second temperature sensor 702, wherein the real-time reading on the fifth pressure sensor 605 is recorded as $P_2$.

In the process of simulating exploitation, the temperature is a constant T; the volume of the inner chamber of the reactor 102 is $V_1$, and the volume of the inner chamber of the thermal insulation gas storage cylinder 305 is $V_2$; and the amount of the natural gas material within the reactor 102 before exploiting can be calculated by the following formula:

$$P_1 V_1 = Z n_1 R T$$

In the formula, $P_1$ is the pressure within the reactor 102 before exploiting, $V_1$ is the volume of the inner chamber of the reactor 102, Z is the corresponding compression factor, $n_1$ is the amount of the natural gas within the reactor 102 before exploiting, and T is the system temperature.

The amount of the natural gas material in the exploitation process can be calculated by the formula:

$$P_2 (V_1 + V_2) = Z n_2 R T$$

In the formula, $P_2$ is the system pressure in the exploitation process, $V_1$ is the volume of the inner chamber of the reactor 102, $V_2$ is the volume of the inner chamber of the thermal insulation gas storage cylinder 305, Z is the corresponding compression factor, $n_2$ is the amount of the natural gas material in the exploitation process, and T is the system temperature.

The amount of the natural gas material generated in the exploitation process is:

$$\Delta n = n_2 - n_1$$

In the formula, $\Delta n$ is the amount of the natural gas material generated in the exploitation process.

When the hydrate is exploited using the pressure-reduction process, the decomposition rate of the hydrate is:

$$u = \frac{d \Delta n}{dt}$$

In the formula, u is the real-time decomposition rate of the hydrate, and t is the time used for exploiting the hydrate.

Meanwhile, by using the real-time data recorded by the impedance sensor 111, analyzing the decomposition status of the hydrate on the axial and radial direction in the computer data processing system, so as to draw a real-time decomposition area prediction diagram; Until the reading of the impedance sensor 111 is stable, i.e., the decomposition of the hydrate is stable, closing the valve on the three-way valve 306 that is connected with the reactor 102 and the thermal insulation gas storage cylinder 305, and closing the slurry pump 108.

Changing the pressure reduction amplitude using a pressure regulator 301, and preferably selecting the pressure parameter of hydrate pressure-reduction exploitation process.

Changing the slurry property and flow rate, and exploring the influence of the slurry circulation on the hydrate pressure-reduction exploitation process in the drilling process.

Changing the ion type and concentration of the solution within the liquid communicating vessel in the liquid injection apparatus 206, and exploring the influence of different ions and concentrations on the hydrate pressure-reduction exploitation process.

Simulating a hydrate heat-injection exploitation process under a slurry circulation condition includes the specific steps as follows:

After simulating generation of the hydrate, recording the reading of the first pressure sensor 601 as $P_1$, opening the power supply of the weighing apparatus 304, and returning to zero; opening a valve on the three-way valve 306 that is connected with the reactor 102 and the gas-liquid separator apparatus 302, regulating the pressure regulating valve 301 so that the reading of the first pressure sensor 601 is kept as the constant $P_1$, and collecting the discharged gas after gas-liquid separation using a drainage method.

Opening the slurry pump 108 to form the slurry circulation system.

Opening the fourth control valve 504, turning on the power supply of the heating apparatus 208, setting the preset temperature for preheating; turning on the power supply of a constant pressure and constant speed pump 207, and setting a pressure and flow rate parameter for heat injection; recording the real-time reading of the weighing apparatus 304 as $m_3$ using the computer data processing system.

Where the reading $m_3$ of the weighing apparatus 304 can be converted into the volume of the liquid discharged by using the drainage method through the following formula:

$$V_3 = \frac{m_3}{\rho_3}$$

In the formula, $V_3$ is the volume of the discharged liquid; $m_3$ is the mass of the discharged liquid; and $P_3$ is the density of the discharged liquid.

The volume of the discharged gas after separation is:

$$V_4 = V_3$$

In the formula, $V_4$ is the volume of the discharged gas after separation.

The amount of the gas material discharged after separation can be calculated by the following formula:

$$n_4 = \frac{V_4 \cdot \rho_4}{M_4}$$

In the formula, $n_4$ is the amount of the gas material discharged after separation; $P_4$ is the density of the gas discharged after separation; and $M_4$ is the relative molecular mass of the gas discharged after separation.

The decomposition rate of the hydrate can be calculated by the following formula:

$$u = \frac{dn_4}{dt}$$

In the formula, u is the real-time decomposition rate of the hydrate; $n_4$ is the amount of the gas material discharged after separation; and t is the time used for exploiting the hydrate.

Meanwhile, by using the real-time data recorded by the impedance sensor 111, analyzing the decomposition of the hydrate on the axial and radial direction in the computer data processing system, so as to draw a real-time decomposition area prediction diagram; Until the reading of the impedance sensor 111 is stable, i.e., the hydrate is decomposed completely, closing the power supplies of the heating apparatus 208 and the constant pressure and constant speed pump 207; closing the fourth control valve 504, the valve on the three-way valve 306 that is connected with the reactor 102 and the gas-liquid separator apparatus 302, and the slurry pump 108.

Changing the heat-injection temperature using the heating apparatus 208, changing the heat-injection pressure and the flow rate using the constant pressure and constant speed pump 207, and preferably selecting the parameters such as temperature, pressure, flow rate and the like of the hydrate heat-injection exploitation process.

Changing the slurry property and flow rate, and exploring the influence of the slurry circulation on the hydrate heat-injection exploitation process.

Changing the ion type and concentration of the solution within the liquid communicating vessel in the liquid injection apparatus 206, and exploring the influence of different ions and concentrations on the hydrate heat-injection exploitation process.

Simulating a hydrate methane-displaced-with-carbon dioxide exploitation process under a slurry circulation condition includes the specific steps as follows:

After simulating generation of the hydrate, recording the reading of the first pressure sensor 601 as $P_1$, and opening the slurry pump 108 to form a slurry circulation system.

Opening the second pin valve 802 and the third control valve 503, turning on the power supply of the gas booster pump 205, setting the pressure to the preset value, and simulating a hydrate methane-displaced-with-carbon dioxide exploitation process; meanwhile, by using the real-time data recorded by the impedance sensor 111, analyzing the decomposition status of the hydrate on the axial and radial directions in the computer data processing system, so as to draw a real-time decomposition area prediction diagram until the reading of the impedance sensor 111 is stable, i.e., the hydrate is decomposed completely; recording the time t used for reaction; closing the second pin valve 802 and the third control valve 503, and turning off the power supply of the gas booster pump 205.

Opening the valve on the three-way valve 306 that is connected with the reactor 102 and the thermal insulation gas storage cylinder 305 so that the thermal insulation gas storage cylinder 305 is communicated with the inner chamber of the reactor 102; observing and recording readings on the first pressure sensor 601, the fourth pressure sensor 604, the fifth pressure sensor 605 and the second temperature sensor 702 until the readings are stable, wherein the reading on the fifth pressure sensor 605 is recorded as $P_3$.

Closing the valve on the three-way valve 306 that is connected with the reactor 102 and the thermal insulation gas storage cylinder 305; injecting a sufficient quantity of NaOH solution into the thermal insulation gas storage cylinder 305 to absorb carbon dioxide in the mixed gas until the reaction is complete; and recording the reading read on the fifth pressure sensor 605 as $P_4$.

In the process of simulating exploitation, the temperature is a constant T; the volume of the inner chamber of the reactor 102 is $V_1$, and the volume of the inner chamber of the thermal insulation gas storage cylinder 305 is $V_2$; and the amount of the natural gas material within the reactor 102 before exploiting can be calculated by the following formula:

$$P_1 V_1 = Z n_1 RT$$

In the formula, $P_1$ is the pressure within the reactor 102 before exploiting, $V_1$ is the volume of the inner chamber of the reactor 102, Z is the corresponding compression factor, $n_1$ is the amount of the natural gas within the reactor 102 before exploiting, and T is the system temperature.

The amount of the mixed gas material of methane and carbon dioxide after exploiting can be calculated by the following formula:

$$P_3(V_1+V_2) = Z n_5 RT$$

In the formula, $P_3$ is the system pressure after exploiting, $V_1$ is the volume of the inner chamber of the reactor 102, $V_2$ is the volume of the inner chamber of the thermal insulation gas storage cylinder 305, Z is the corresponding compression factor, $n_5$ is the amount of the mixed gas material of methane and carbon dioxide after exploiting, and T is the system temperature.

The amount of the mixed gas material in the thermal insulation gas storage cylinder 305 after exploiting can be calculated by the following formula:

$$\frac{n_6}{n_5} = \frac{V_2}{V_1 + V_2}$$

In the formula, $V_1$ is the volume of the inner chamber of the reactor 102, $V_2$ is the volume of the inner chamber of the thermal insulation gas storage cylinder 305, $n_5$ is the amount of the mixed gas material of methane and carbon dioxide after exploiting, and $n_6$ is the amount of the mixed gas material in the thermal insulation gas storage cylinder 305 after exploiting.

The amount of the methane material in the thermal insulation gas storage cylinder 305 after exploiting can be calculated by the following formula:

$$P_4V_2=Zn_7RT$$

In the formula, $V_2$ is the volume of the inner chamber of the thermal insulation gas storage cylinder 305, Z is the corresponding compression factor, $n_7$ is the amount of the methane material in the thermal insulation gas storage cylinder 305 after exploiting, $P_4$ is the system pressure within the thermal insulation gas storage cylinder 305 after exploiting and removing carbon dioxide.

The total amount of the natural gas material after exploiting is:

$$n_8 = n_5 \frac{n_7}{n_6}$$

In the formula, $n_8$ is the total amount of the methane material after exploiting, $n_5$ is the amount of the mixed gas material of methane and carbon dioxide after exploiting, $n_6$ is the amount of the mixed gas material in the thermal insulation gas storage cylinder 305 after exploiting, and $n_7$ is the amount of the methane material in the thermal insulation gas storage cylinder 305 after exploiting.

The amount of the natural gas material generated in the exploitation is:

$$\Delta n = n_8 - n_1$$

In the formula, $\Delta n$ is the amount of the natural gas material generated in the exploitation.

The decomposition rate of the hydrate exploitation using a displacement process is:

$$v = \frac{\Delta n}{t}$$

In the formula, v is the decomposition rate of the hydrate displacement exploitation process, and t is the time used for the hydrate displacement exploitation process.

Changing the carbon dioxide injection pressure by the gas booster pump 205, and preferably selecting the pressure parameter of the hydrate exploited by the displacement process.

Changing the slurry property and flow rate, and exploring the influence of the slurry circulation on the hydrate displacement exploitation process.

Changing the ion type and concentration of the solution within the liquid communicating vessel in the liquid injection apparatus 206, and exploring the influence of different ions and concentrations on the hydrate displacement exploitation process.

What is claimed is:

1. An apparatus for monitoring hydrate decomposition area under different drilling and production processes, comprising a reaction unit, an auxiliary unit and a determination unit, wherein the reaction unit is configured to simulate hydrate storage layer environment to provide a place for generation and decomposition of hydrate, to simulate a hydrate heat-injection exploitation process, a hydrate pressure-reduced exploitation process and a hydrate $CO_2$ displacement exploitation process, and also to analyze hydrate decomposition status at various areas by calculating hydrate decomposition rate, so as to evaluate and optimize the drilling and production process; wherein the auxiliary unit is configured to provide a gas source and a liquid source for the reaction unit, and to simulate different hydrate drilling and production processes; and wherein the determination unit is configured to measure the hydrate decomposition rate in different drilling and production processes; wherein, the determination unit comprises: a pressure regulating valve, a gas-liquid separator apparatus, a closed liquid drainage container, a weighing apparatus, a pre-vacuumed thermal insulation gas storage cylinder, and a three-way valve; an air outlet is connected with the three-way valve through a transmission pipeline; a fourth pressure sensor and the pressure regulating valve are installed orderly on the transmission pipeline in a direction from the air outlet to the three-way valve; the fourth pressure sensor is configured to measure real-time pressure within the reactor when discharging gas; the pressure regulating valve is configured to be regulated to keep the real-time pressure within the reactor at a set of predetermined values; flow and flow direction of the fluid are controlled through the three-way valve; the gas-liquid separator apparatus is connected with the three-way valve; the three-way valve is configured to guide the discharged fluid to the gas-liquid separator apparatus for gas-liquid separation; a liquid hole is formed on a lower part of the gas-liquid separator apparatus; the liquid hole is connected with the third liquid storage container through the transmission pipeline; the third liquid storage container contains the separated liquid; an air hole is disposed on an upper end of the gas-liquid separator apparatus; the air hole is connected with a top end of the closed liquid drainage container through the transmission pipeline; the closed liquid drainage container is connected with the fourth liquid storage container through the transmission pipeline; the transmission pipeline stretches into an inner chamber of the closed liquid drainage container and approaches to bottom; the fourth liquid storage container is placed on the weighing apparatus; the weighing apparatus is connected with a computer data processing system; the closed liquid drainage container measures a volume of the gas after gas-liquid separation through a drainage process; the fourth liquid storage container contains water discharged through the drainage process; the weighing apparatus measures mass of the discharged water; the computer data processing system is used to collect, store and analyze the real-time mass data; the pre-vacuumed thermal insulation gas storage cylinder is connected with the three-way valve through the transmission pipeline; the thermal insulation gas storage cylinder is equipped with a second temperature sensor and a fifth pressure sensor; a volume of the thermal insulation gas storage cylinder is configured to be unchanged so as to change the pressure of the system and simulate the hydrate pressure-reduction exploitation process; and the second temperature sensor and the fifth pressure sensor measure real-time temperatures and pressures within the thermal insulation gas storage cylinder.

2. The apparatus for monitoring hydrate decomposition area under different drilling and production processes according to claim 1, wherein the reaction unit comprises: an incubator, a reactor, a drill pipe and a first liquid storage container; the reactor is disposed inside the incubator; a support is disposed on top of the incubator for clamping the drill pipe; the reactor contains required sand; and temperature of the incubator is controllable to stimulate the storage layer environment with different temper ores.

3. The apparatus for monitoring hydrate decomposition area under different drilling and production processes according to claim 2, wherein an air inlet, a liquid inlet and an air outlet are formed on a top end of the reactor with the air outlet located at center and the air inlet and the liquid inlet located on two sides of the air outlet; and the drill pipe enters into the reactor through the air outlet.

4. The apparatus for monitoring hydrate decomposition area under different drilling and production processes according to claim 3, wherein, the first liquid storage container is connected with a top end of the drill pipe through a transmission pipeline; a slurry pump, and flow gauge and a check valve are orderly disposed on the transmission pipeline in a direction from the first liquid storage container to the drill pipe; and the air outlet is connected with the first liquid storage container through a return pipeline.

5. The apparatus for monitoring hydrate decomposition are under different drilling and production processes according to claim 4, wherein, the reactor is provided with impedance sensors, a first pressure sensor and a first temperature sensor that are all connected with a computer data processing system; the impedance sensors are longitudinally and uniformly distributed inside the reactor in three layers with 17 in each layer; one of the impedance sensors is disposed at center of each layer; eight radial directions extend by taking the impedance sensor at the center as the starting point; the adjacent radial directions form an angle of 45 degrees; and two impedance sensors are disposed equidistantly in each radial direction except the one at the center, such that the remaining impedance sensors except the one at the center are located on two concentric circles.

6. The apparatus for monitoring hydrate decomposition are under different drilling and production processes according to claim 5, wherein, the auxiliary unit comprises a vacuum pump, a vacuum gauge, a high pressure methane gas cylinder, a high pressure carbon dioxide gas cylinder, a gas booster pump, a liquid injection apparatus, a second liquid storage container and a heating apparatus; the vacuum pump is connected with the air inlet through a pipeline; a first control valve and the vacuum gauge are installed orderly on the pipeline in a direction from the vacuum pump to the air inlet; the gas booster pump is connected with the air inlet through the transmission pipeline; a third control valve and a third pressure sensor are installed orderly on the transmission pipeline in a direction from the gas booster pump to the air inlet; the high pressure methane gas cylinder is provided with a first pin valve that is connected with the gas booster pump through the transmission pipeline; and the high pressure carbon dioxide gas cylinder is provided with a second pin valve that is connected with the gas booster pump through the transmission pipeline.

7. The apparatus for monitoring hydrate decomposition area under different drilling and production processes according to claim 6, wherein, the liquid injection apparatus is connected with the liquid inlet on the reactor through the transmission pipeline; a second pressure sensor and a second control valve are installed orderly on the transmission pipeline in a direction from the liquid injection apparatus to the liquid inlet; the liquid injection apparatus consists of a liquid communicating vessel and a manual pump; the liquid communicating vessel contains a set disposing solution; and the disposing solution is injected into the reactor through the manual pump.

8. The apparatus for monitoring hydrate decomposition are under different drilling and production processes according to claim 7, wherein, the second liquid storage container is connected with top end of the drill pipe through the transmission pipeline; and a constant pressure and constant speed pump, a fourth control valve and the heating apparatus are installed orderly on the transmission pipeline in a direction from the second liquid storage container to the drill pipe.

9. A method for monitoring hydrate decomposition area under different drilling and production processes using the apparatus for monitoring hydrate decomposition area under drilling and production processed of claim 8 to stimulate generation of hydrate, a hydrate pressure-reduction exploitation process under a slurry circulation condition, a hydrate heat-injection exploitation process under the slurry circulation process and a hydrate methane-displaced-with-carbon dioxide exploitation process under the slurry circulation condition, wherein simulating generation of hydrate comprises steps of:

placing quantitative sand and stone in the reactor according to the set proportion and distribution to stimulate the corresponding storage layer environment, closing all the valves of the apparatus;

opening the first control valve and the vacuum pump to pump out the gas in the inner chamber of the reactor until the reading of the vacuum gage is negative;

closing the vacuum pump and the first control valve;

preparing an ionic solution with a specified concentration and putting it in the liquid communicating vessel of the liquid injection apparatus;

opening the second control valve; rotating the manual pump in the liquid injection apparatus to inject the prepared solution into the reactor; during the injection process, adjusting the rotating speed of the manual pump by observing the pressure reading of the second pressure sensor, observing and recording the volume reading on the liquid communicating vessel until the pressure reading of the second pressure sensor and the volume reading of the liquid communicating vessel reach the preset value; stopping rotating the manual pump and closing the second control valve;

turning on a power supply of the incubator, adjusting the temperature to the preset value, and heating the reactor until the actual reading change of the temperature of the incubator is less than plus or minus 0.01° C.;

opening the first pin valve and the third control valve, opening the gas booster pump, setting a specified pressure, pumping the methane gas within the high pressure methane gas cylinder to the reactor, observing and recording the real-time readings of the first pressure sensor, the third pressure sensor, the impedance sensor and the first temperature sensor; continuing gas injection until the readings of the first pressure sensor and the third pressure sensor reach the preset value and the readings of the impedance sensor and the first temperature sensor become stable, i.e., after the hydrate within the reactor is generated completely under the preset pressure, closing the first pin valve and the third control valve and closing the gas booster pump;

wherein simulating a hydrate pressure-reduction exploitation process under a slurry circulation condition comprises steps of:

after simulating generation of the hydrate, recording the reading of the first pressure sensor as $P_1$, and opening the slurry pump to form a slurry circulation system;

opening a valve on the three-way valve that is connected with the reactor and the thermal insulation gas storage cylinder so that the thermal insulation gas storage cylinder is communicated with the inner chamber of the reactor, thereby realizing a pressure reduction function; observing and recording readings on the fourth pressure sensor, the fifth pressure sensor and the second temperature sensor, wherein the real-time reading on the fifth pressure sensor is recorded as $P_2$;

in the process of simulating exploitation, the temperature is a constant T; the volume of the inner chamber of the reactor is $V_1$, and the volume of the inner chamber of the thermal insulation gas storage cylinder is $V_2$; and the amount of the natural gas material within the reactor before exploiting is calculated by the following formula:

$$P_1V_1 = Zn_1RT$$

where $P_1$ is the pressure within the reactor before exploiting, $V_1$ is the volume of the inner chamber of the reactor, Z is the corresponding compression factor, $n_1$ is the amount of the natural gas material within the reactor before exploiting, and T is the system temperature;

the amount of the natural gas material in the exploitation process is calculated by the formula:

$$P_2(V1+V2) = Zn2RT$$

where $P_2$ is the system pressure in the exploitation process, $V_1$ is the volume of the inner chamber of the reactor, $V_2$ is the volume of the inner chamber of the thermal insulation gas storage cylinder, $n_2$ is the amount of the natural gas material in the exploitation process, and T is the system temperature;

the amount of the natural gas material generated in the exploitation process is:

$$\Delta n = n_2 - n_1$$

where $\Delta n$ is the amount of the natural gas material generated in the exploitation process;

when the hydrate is exploited using the pressure reduction process, the decomposition rate of the hydrate is:

$$u = \frac{d\Delta n}{dt}$$

where u is the real-time decomposition rate of the hydrate, and t is the time used for exploiting the hydrate;

by using the real-time data recorded by the impedance sensor, analyzing the decomposition status of the hydrate on the axial and radial directions the computer data processing system, so as to draw a real time decomposition area prediction diagram; until the reading of the impedance sensor is stable, i.e., the decomposition of the hydrate is stable, closing the valve on the three-way valve that is connected with the reactor and the thermal insulation gas storage cylinder, and closing the slurry pump;

changing the pressure reduction amplitude using the pressure regulator;

changing the slurry property and flow rate, and exploring the influence of the slurry circulation on the hydrate pressure-reduction exploitation process in the drilling process;

changing the ion type and concentration of the solution within the liquid communicating vessel in the liquid injection apparatus, and exploring the influence of different ions and concentrations on the hydrate pressure-reduction exploitation process;

wherein simulating a hydrate heat-injection exploitation process under a slurry circulation condition comprises steps of:

after simulating generation of the hydrate, recording the reading of the first pressure sensor as $P_1$, opening the power supply of a weighing apparatus, and returning to zero; opening a valve on the three-way valve that is connected with the reactor and the gas-liquid separator apparatus, regulating a pressure regulating valve so that the reading of the first pressure sensor is kept as the constant P1, and collecting the discharged gas after gas-liquid separation using a drainage process;

opening the slurry pump to form the slurry circulation system;

opening the fourth control valve, turning on the power supply of the heating apparatus, setting the preset temperature for preheating; turning on the power supply of the constant pressure and constant speed pump, and setting a pressure and flow rate parameter for heat-injection; recording the real-time reading of the weighing apparatus as $m_3$ using the computer data processing system;

wherein the reading $m_3$ of the weighing apparatus is converted into the volume of the liquid discharged by using the drainage process through the following formula:

$$V_3 = \frac{m_3}{\rho_3}$$

where $V_3$ is the volume of the discharged liquid; $m_3$ is the mass of the discharged liquid; and $P_3$ is the density of the discharged liquid; the volume of the discharged gas after separation is:

$$V_4 = V_3$$

where $V_4$ is the volume of the discharged gas after separation;

the amount of the gas material discharged after separation is calculated by the following formula:

$$n_4 = \frac{V_4 \cdot \rho_4}{M_4}$$

where $n_4$ is the amount of the gas material discharged after separation; $P_4$ is the density of the gas discharged after separation; and $M_4$ is the relative molecular mass of the gas discharged after separation;

the decomposition rate of the hydrate is calculated by the following formula:

$$u = \frac{dn_4}{dt}$$

where u is the real-time decomposition rate of the hydrate; $n_4$ is the amount of the gas material discharged after separation; and t is the time used for exploiting the hydrate;

by using the real-time data recorded by the impedance sensor, analyzing the decomposition of the hydrate on the axial and radial direction in the computer data processing system, so as to draw a real-time decomposition area prediction diagram; until the reading of the impedance sensor is stable, that the hydrate is decomposed completely, closing the power supplies of the heating apparatus and the constant pressure and constant speed pump; closing the fourth control valve, the valve on the three-way valve that is connected with the reactor and the gas-liquid separator apparatus, and the slurry pump;

changing the heat-injection temperature using the heating apparatus, changing the heat-injection pressure and the flow rate using the constant pressure and constant speed pump;

changing the slurry property and flow rate, and exploring the influence of the slurry circulation on the hydrate heat-injection exploitation process;

changing the ion type and concentration of the solution within the liquid communicating vessel in the liquid injection apparatus, and exploring the influence of different ions and concentrations on the hydrate heat-injection exploitation process;

wherein simulating a hydrate methane-displaced-with-carbon dioxide exploitation process under a slurry circulation condition comprises steps of:

after simulating generation of the hydrate, recording the reading of the first pressure sensor as $P_1$, and opening the slurry pump to form a slurry circulation system;

opening the second pin valve and the third control valve, turning on the power supply of the gas booster pump, setting the pressure to the preset value, and simulating a hydrate methane-displaced-with-carbon dioxide exploitation process; meanwhile, by using the real-time data recorded by the impedance sensor, analyzing the decomposition status of the hydrate on the axial and radial directions in the computer data processing system, so as to draw a real-time decomposition area prediction diagram until the reading of the impedance sensor is stable, i.e., the hydrate is decomposed completely; recording the time t used for reaction; closing the second pin valve and the third control valve, and turning off the power supply of the gas booster pump;

opening the valve on the three-way valve that is connected with the reactor and the thermal insulation gas storage cylinder so that the thermal insulation gas storage cylinder is communicated with the inner chamber of the reactor; observing and recording readings on the first pressure sensor, the fourth pressure sensor, the fifth pressure sensor and the second temperature sensor until the readings are stable, wherein the reading on the fifth pressure sensor is recorded as $P_3$;

closing the valve on the three-way valve that is connected with the reactor and the thermal insulation gas storage cylinder; injecting a sufficient quantity of NaOH solution into the thermal insulation gas storage cylinder to absorb carbon dioxide in the mixed gas until the reaction is complete; and recording the reading read on the fifth pressure sensor as $P_4$;

in the process of simulating exploitation, the temperature is a constant T; the volume of the inner chamber of the reactor 102 is $V_1$, and the volume of the inner chamber of the thermal insulation gas storage cylinder is $V_2$; and the amount of the natural gas material within the reactor before exploiting is calculated by the following formula:

$$P_1 V_1 = Z n_1 R T$$

where $P_1$ is the pressure within the reactor before exploiting, $V_1$ is the volume of the inner chamber of the reactor, $n_1$ is the amount of the natural gas material within the reactor before exploiting, and T is the system temperature;

the amount of the mixed gas material of methane and carbon dioxide after exploiting is calculated by the following formula:

$$P_3(V_1+V_2) = Z n_5 R T$$

where $P_3$ is the system pressure after exploiting, $V_1$ is the volume of the inner chamber of the reactor, $V_2$ is the volume of the inner chamber of the thermal insulation gas storage cylinder, $n_5$ is the amount of the mixed gas material of methane and carbon dioxide after exploiting, and T is the system temperature;

the amount of the mixed gas material in the thermal insulation gas storage cylinder after exploiting is calculated by the following formula:

$$\frac{n_6}{n_5} = \frac{V_2}{V_1 + V_2}$$

where $V_1$ is the volume of the inner chamber of the reactor, $V_2$ is the volume of the inner chamber of the thermal insulation gas storage cylinder, $n_5$ is the amount of the mixed gas material of methane and carbon dioxide after exploiting, and $n_6$ is the amount of the mixed gas material in the thermal insulation gas storage cylinder after exploiting;

the amount of the methane material in the thermal insulation gas storage cylinder after exploiting is calculated by the following formula:

$$P_4 V_2 = Z n_7 R T$$

where $V_2$ is the volume of the inner chamber of the thermal insulation gas storage cylinder, $n_7$ is the amount of the methane material in the thermal insulation gas storage cylinder after exploiting, $P_4$ is the system pressure within the thermal insulation gas storage cylinder after exploiting and removing carbon dioxide;

the total amount of the natural gas material after exploiting is:

$$n_8 = n_5 \frac{n_7}{n_6}$$

where $n_8$ is the total amount of the methane material after exploiting, $n_5$ is the amount of the mixed gas material of methane and carbon dioxide after exploiting, $n_6$ is the amount of the mixed gas material in the thermal insulation gas storage cylinder after exploiting, and $n_7$ is the amount of the methane material in the thermal insulation gas storage cylinder after exploiting;

the amount of the natural gas material generated in the exploitation is:

$$\Delta n = n_8 - n_1$$

where $\Delta n$ is the amount of the natural gas material generated in the exploitation;

the decomposition rate of the hydrate exploitation using a displacement process is:

$$v = \frac{\Delta n}{t}$$

where v is the decomposition rate of the hydrate displacement exploitation process, and t is the time used for the hydrate displacement exploitation process;

changing the carbon dioxide injection pressure by the gas booster pump;

changing the slurry property and flow rate, and exploring the influence of the slurry circulation on the hydrate displacement exploitation process;

changing the ion type and concentration of the solution within the liquid communicating vessel in the liquid injection apparatus, and exploring the influence of different ions and concentrations on the hydrate displacement exploitation process.

* * * * *